(12) United States Patent
Garkavtsev et al.

(10) Patent No.: US 11,351,144 B2
(45) Date of Patent: Jun. 7, 2022

(54) COMPOUNDS FOR INHIBITING SECRETORY LEUKOCYTE PROTEASE INHIBITOR (SLPI)

(71) Applicant: The General Hospital Corporation, Boston, MA (US)

(72) Inventors: Igor Garkavtsev, Cambridge, MA (US); Rakesh K. Jain, Wellesley, MA (US)

(73) Assignee: The General Hospital Corporation, Boston, MA (US)

( * ) Notice: Subject to any disclaimer, the term of this patent is extended or adjusted under 35 U.S.C. 154(b) by 55 days.

(21) Appl. No.: 16/754,912

(22) PCT Filed: Oct. 9, 2018

(86) PCT No.: PCT/US2018/054957
§ 371 (c)(1),
(2) Date: Apr. 9, 2020

(87) PCT Pub. No.: WO2019/074895
PCT Pub. Date: Apr. 18, 2019

(65) Prior Publication Data
US 2021/0196666 A1    Jul. 1, 2021

Related U.S. Application Data

(60) Provisional application No. 62/569,688, filed on Oct. 9, 2017.

(51) Int. Cl.
| | | |
|---|---|---|
| A61K 31/16 | (2006.01) | |
| A61P 35/00 | (2006.01) | |
| A61K 31/245 | (2006.01) | |
| A61P 35/04 | (2006.01) | |
| A61K 45/06 | (2006.01) | |

(52) U.S. Cl.
CPC ............ *A61K 31/245* (2013.01); *A61K 45/06* (2013.01); *A61P 35/04* (2018.01)

(58) Field of Classification Search
CPC ................................ A61K 31/16; A61P 35/00
USPC ........................................................ 514/622
See application file for complete search history.

(56) References Cited

U.S. PATENT DOCUMENTS

| 2009/0306078 A1 | 10/2009 | Lee et al. |
| 2014/0141986 A1 | 5/2014 | Spetzler et al. |
| 2015/0157584 A1 | 6/2015 | Guan et al. |

OTHER PUBLICATIONS

Alvarez-Fernández & Medema., "Novel functions of FoxM1: from molecular mechanisms to cancer therapy," Front. Oncol., Mar. 2013, 3:30.
Ameshima et al., "Increased secretory leukoprotease inhibitor in patients with nonsmall cell lung carcinoma," Cancer, Oct. 2000, 89(7):1448-1456.
Amiano et al., "Anti-tumor effect of SLPI on mammary but not colon tumor growth," J. Cell. Physiol, Feb. 2013, 228(2):469-475.
Bianchini et al., "Triple-negative breast cancer: challenges and opportunities of a heterogeneous disease," Nat. Rev. Clin. Oncol., Nov. 2016, 13(11):674-690.
Bresalier et al., "Mucin production by human colonic carcinoma cells correlates with their metastatic potential in animal models of colon cancer metastasis," J. Clin. Invest., Mar. 1991, 87(3):1037-1045.
Chaffer & Weinberg, "A Perspective on Cancer Cell Metastasis," Science, Mar. 2011, 331(6024):1559-1564.
Chen et al, "Breast Tumor Microenvironment: Proteomics Highlights the Treatments Targeting Secretomel," J. Proteome Res., Apr. 2008, 7(4):1379-1387.
Cheng et al., "Overexpression of a secretory leukocyte protease inhibitor in human gastric cancer," Int. J. Cancer, Oct. 2008, 123(8):1787-1796.
Choi et al., "Secretory leukocyte protease inhibitor is associated with MMP-2 and MMP-9 to promote migration and invasion in SNU638 gastric cancer cells," Int. J. Mol. Med., Oct. 2011, 28(4):527-534.
Cimino et al., "Identification of new genes associated with breast cancer progression by gene expression analysis of predefined sets of neoplastic tissues," Int. J. Cancer, Sep. 2008, 123:1327-1338.
Cordes et al., "The level of secretory leukocyte protease inhibitor is decreased in metastatic head and neck squamous cell carcinoma," Int. J. Cancer, Jul. 2011, 39(1):185-191.
Dai et al., "Aberrant FoxM1B expression increases matrix metalloproteinase-2 transcription and enhances the invasion of glioma cells," Oncogene, Sep. 2007, 26(4):6212-6219.
Devoogdt et al., "Secretory leukocyte protease inhibitor promotes the tumorigenic and metastatic potential of cancer cells," Proc. Natl. Acad. Sci. USA., May 2003, 100(10):5778-5582.
Gartel, "FOXM1 in cancer: interactions and vulnerabilities," Cancer Res., Jun. 2017, 77(12):3135-3139.
Gunawardane et al., "Novel role for PDEF in epithelial cell migration and invasion," Cancer Res., Dec. 2005, 65(24):11572-11580.
Győrffy et al., "Online survival analysis software to assess the prognostic value of biomarkers using transcriptomic data in non-small-cell lung cancer," PLoS One, Dec. 2013, 8(12):e82241.
Jiang et al., "Overexpression of FOXM1 is associated with metastases of nasopharyngeal carcinoma," Ups. J. Med. Sci., Nov. 2014, 119(4):324-332.
Kalinichenko et al., "Foxm1b transcription factor is essential for development of hepatocellular carcinomas and is negatively regulated by the p19ARF tumor suppressor," Genes Dev., Apr. 2004, 18(7):830-850.
Kluger et al., "Using a xenograft model of human breast cancer metastasis to find genes associated with clinically aggressive disease," Cancer Res., Jul. 2005, 65(13):5578-5587.
Liu et al., "Expression of secretory leukocyte protease inhibitor detected by immunohistochemistry correlating with prognosis and metastasis in colorectal cancer," World J. Surg. Oncol., Dec. 2014, 12(1):369.

(Continued)

*Primary Examiner* — Raymond J Henley, III
(74) *Attorney, Agent, or Firm* — Fish & Richardson P.C.

(57) ABSTRACT

This invention relates to compounds that are useful for inhibiting the secretion of secretory leukocyte protease inhibitor (SLPI) in a subject. Methods of inhibiting metastasis of cancer and methods of treating cancer in a subject are also provided.

18 Claims, 7 Drawing Sheets

(56) References Cited

OTHER PUBLICATIONS

Lorusso & Rüegg, "New insights into the mechanisms of organ-specific breast cancer metastasis," Semin. Cancer Biol., Jun. 2012, 22(3):226-233.

McNeely et al., "Secretory leukocyte protease inhibitor: a human saliva protein exhibiting anti-human immunodeficiency virus 1 activity in vitro," J. Clin. Inves., Jul. 1995, 96(1):456-464.

PCT International Preliminary Report on Patentability in International Appln. No. PCT/US2018/054957, dated Apr. 14, 2020, 7 pages.

PCT International Search Report and Written Opinion in International Appln. No. PCT/US2018/054957, dated Dec. 7, 2018, 9 pages.

Raychaudhuri & Park., "FoxM1: a master regulator of tumor metastasis," Cancer Res., Jul. 2011, 71(13):4329-4333.

Saba et al., "The role of forkhead box protein m1 in breast cancer progression and resistance to therapy," Int. J. Breast Cancer, Jan. 2016, 2016:9768183.

Sayers et al., "Increased Secretory Leukocyte Protease Inhibitor (SLPI) Production by Highly Metaslalic Mouso Bieasl Cancer Cells," PLOS One, Aug. 2014, 9(8):el04223, 7 pages.

Sledge et al., "Past, present, and future challenges in breast cancer treatment," J. Clin. Oncol., Jul. 2014, 32(19):1979-1986.

Sotiriou et al., "Gene expression profiling in breast cancer: understanding the molecular basis of histologic grade to improve prognosis," J. Natl. Cancer Inst., Feb. 2006, 98(4):262-272.

Sugino et al, "The secretory leukocyte protease inhibitor (SLPI) suppresses cancer cell invasion but promotes blood-borne metastasis via an invasion-independent pathway," J. Pathol., Jun. 2007, 212(2):152-160.

Thompson & Ohlsson, "Isolation, properties, and complete amino acid sequence of human secretory leukocyte protease inhibitor, a potent inhibitor of leukocyte elastase," Proc. Natl. Acad. Sci. USA., Sep. 1986, 83(18):6692-6696.

Uddin et al., "Genome-wide expression analysis of Middle Eastern colorectal cancer reveals FOXM1 as a novel target for cancer therapy," Am. J. Pathol., Feb. 2011, 178(2):537-547.

Wang et al., "The Secretory Leukocyte Protease Inhibitor Is a Type 1 Insulin-Like Growth Factor Receptor-Regulated Protein that Protects against Liver Metastasis by Attenuating the Host Proinflammatory Response," Cancer Res.,Mar. 2006, 66(6):3062-3070.

Wierstra & Alves., "Transcription factor FOXM1c is repressed by RB and activated by cyclin D1/Cdk4," Biol. Chem. Jul. 2006, 387(7):949-962.

Zhang et al., "Secretory leukocyte protease inhibitor mediates proliferation of human endometrial epithelial cells by positive and negative regulation of growth-associated genes," J. Biol. Chem., Aug. 2002, 277(33):29999-30009.

Zhu et al., "Conversion of proepithelin to epithelins: roles of SLPI and elastase in host defense and wound repair," Cell, Dec. 2002, 111(6):867-878.

3-{[(2-chlorophenoxy)acetyl]amino}benzoate

COMPOUNDS FOR INHIBITING SECRETORY LEUKOCYTE PROTEASE INHIBITOR (SLPI)

CROSS-REFERENCE TO RELATED APPLICATIONS

This application is a § 371 National Stage Application of PCT/US2018/054957, filed Oct. 9, 2018, which claims the benefit of U.S. Provisional Application Ser. No. 62/569,688, filed Oct. 9, 2017, the disclosure of which is incorporated herein by reference in its entirety.

FEDERALLY SPONSORED RESEARCH OR DEVELOPMENT

This invention was made with Government support under the Federal Share Proton Beam Program and Grant No. CA169616, awarded by the National Institutes of Health. The Government has certain rights in the invention.

TECHNICAL FIELD

This invention relates to compounds that are useful for inhibiting the secretion of secretory leukocyte protease inhibitor (SLPI) in a subject.

BACKGROUND

Secretory leukocyte protease inhibitor (SLPI) has been implicated in the progression and metastasis of certain cancers. The function of SLPI has been the subject of extensive investigation since it exerts pleiotropic activities in multiple biological contexts. For example, SLPI has been reported to be involved in the inhibition of inflammation, the modulation of immunological responses, and the promotion of cell proliferation (see e.g., Zhang et al, *J. Biol. Chen.* 2002, 277:29999-30009; McNeely et al, *J. Clin. Inves.* 1995, 96:456-464: and Zhu et al, Cell, 2002, 111:867-878).

SUMMARY

The present application provides, inter alia, a method of inhibiting metastasis of a cancer in a subject, comprising administering to the subject a compound of Formula I:

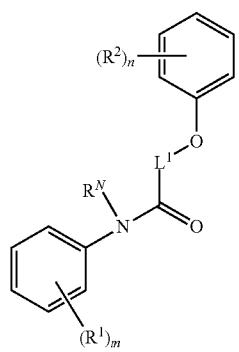

or a pharmaceutically acceptable salt thereof, wherein:
$R^N$ is selected from the group consisting of H and $C_{1-6}$ alkyl;
$L^1$ is a $C_{1-6}$ alkylene group;
each $R^1$ is independently selected from the group consisting of $C(O)R^a$ and $C(O)OR^a$;
each $R^a$ is independently from the group consisting of H and $C_{1-6}$ alkyl;
each $R^2$ is independently selected from the group consisting halo, $C_{1-6}$ alkyl, $C_{1-6}$ haloalkyl, and $C_{1-6}$ alkoxy;
m is 1 or 2; and
n is 1 or 2.

The present application further provides a method of treating cancer in a subject, comprising administering to the subject a compound of Formula I:

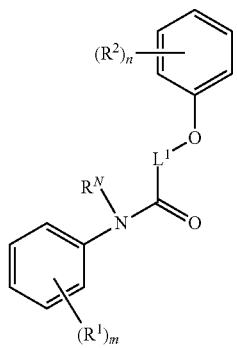

or a pharmaceutically acceptable salt thereof, wherein:
$R^N$ is selected from the group consisting of H and $C_{1-6}$ alkyl;
$L^1$ is a $C_{1-6}$ alkylene group;
each $R^1$ is independently selected from the group consisting of C(O)R and C(O)OR;
each $R^a$ is independently from the group consisting of H and $C_{1-6}$ alkyl;
each $R^2$ is independently selected from the group consisting halo, $C_{1-6}$ alkyl, $C_{1-6}$ haloalkyl, and $C_{1-6}$ alkoxy;
m is 1 or 2; and
n is 1 or 2.

In some embodiments, the cancer is associated with abnormal levels or expression of secretory leukocyte protease inhibitor in the subject. In some embodiments, the cancer is selected from breast cancer, lung cancer, gastric cancer, and colorectal cancer. In some embodiments, the cancer is breast cancer. In some embodiments, the cancer is triple negative breast cancer. In some embodiments, the cancer is lung cancer. In some embodiments, the cancer is non-small cell lung cancer.

The present application further provides a method of inhibiting secretion of secretory leukocyte protease inhibitor in a subject, comprising administering to the subject a compound of Formula I:

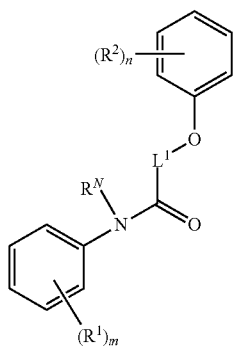

or a pharmaceutically acceptable salt thereof, wherein:
$R^N$ is selected from the group consisting of H and $C_{1-6}$ alkyl;
$L^1$ is a $C_{1-6}$ alkylene group;
each $R^1$ is independently selected from the group consisting of $C(O)R^a$ and $C(O)OR^a$;
each R is independently selected from the group consisting of H and $C_{1-6}$ alkyl;
each $R^2$ is independently selected from the group consisting halo, $C_{1-6}$ alkyl, $C_{1-6}$ haloalkyl, and $C_{1-6}$ alkoxy;
m is 1 or 2; and
n is 1 or 2.

The present application further provides a method of inhibiting expression of secretory leukocyte protease inhibitor in a subject, comprising administering to the subject a compound of Formula I:

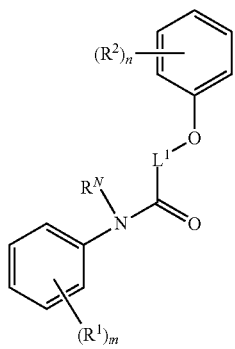

or a pharmaceutically acceptable salt thereof, wherein:
$R^N$ is selected from the group consisting of H and $C_{1-6}$ alkyl;
$L^1$ is a $C_{1-6}$ alkylene group;
each $R^1$ is independently selected from the group consisting of $C(O)R^a$ and $C(O)OR^a$;
each $R^a$ is independently selected from the group consisting of H and $C_{1-6}$ alkyl;
each $R^2$ is independently selected from the group consisting halo, $C_{1-6}$ alkyl, $C_{1-6}$ haloalkyl, and $C_{1-6}$ alkoxy;
m is 1 or 2; and
n is 1 or 2.

The present application further provides a method of inhibiting retinoblastoma (Rb) tumor suppressor protein phosphorylation in a subject, comprising administering to the subject a compound of Formula I:

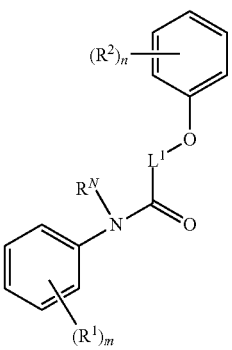

or a pharmaceutically acceptable salt thereof, wherein:
$R^N$ is selected from the group consisting of H and $C_{1-6}$ alkyl;
$L^1$ is a $C_{1-6}$ alkylene group;
each $R^1$ is independently selected from the group consisting of $C(O)R^a$ and $C(O)ORI$;
each $R^a$ is independently selected from the group consisting of H and $C_{1-6}$ alkyl;
each $R^2$ is independently selected from the group consisting halo, $C_{1-6}$ alkyl, $C_{1-6}$ haloalkyl, and $C_{1-6}$ alkoxy;
m is 1 or 2; and
n is 1 or 2.

The present application further provides a method of inhibiting expression of Forkhead box transcriptional factor M1 (FoxM1) in a subject, comprising administering to the subject a compound of Formula I:

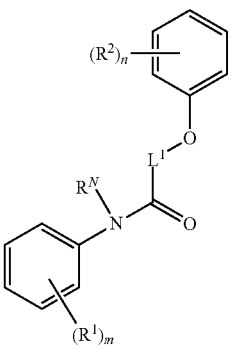

or a pharmaceutically acceptable salt thereof, wherein:
$R^N$ is selected from the group consisting of H and $C_{1-6}$ alkyl;
$L^1$ is a $C_{1-6}$ alkylene group;
each $R^1$ is independently selected from the group consisting of C(O)R and C(O)OR;
each $R^a$ is independently selected from the group consisting of H and $C_{1-6}$ alkyl;
each $R^2$ is independently selected from the group consisting halo, $C_{1-6}$ alkyl, $C_{1-6}$ haloalkyl, and $C_{1-6}$ alkoxy;
m is 1 or 2; and
n is 1 or 2.

The present application further provides a method of inhibiting activation of Forkhead box transcriptional factor M1 (FoxM1) signaling in a subject, comprising administering to the subject a compound of Formula I:

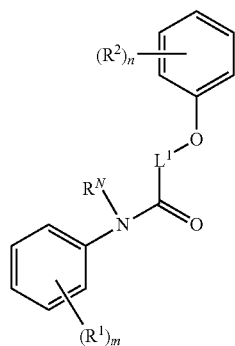

I or a pharmaceutically acceptable salt thereof, wherein:

$R^N$ is selected from the group consisting of H and $C_{1-6}$ alkyl;

$L^1$ is a $C_{1-6}$ alkylene group;

each $R^1$ is independently selected from the group consisting of C(O)R and C(O)OR$^a$;

each $R^a$ is independently selected from the group consisting of H and $C_{1-6}$ alkyl;

each $R^2$ is independently selected from the group consisting halo, $C_{1-6}$ alkyl, $C_{1-6}$ haloalkyl, and $C_{1-6}$ alkoxy;

m is 1 or 2; and n is 1 or 2.

In some embodiments, $R^N$ is H.

In some embodiments, $L^1$ is a $C_{1-3}$ alkylene group. In some embodiments, $L^1$ is methylene.

In some embodiments, each $R^1$ is C(O)OR$^a$. In some embodiments, each $R^a$ is independently selected from the group consisting of H and $C_{3-6}$ alkyl. In some embodiments, each $R^1$ is selected from C(O)OH, C(O)CH$_2$CH$_2$CH$_3$, and C(O)CH$_2$CH$_2$CH$_2$CH$_3$.

In some embodiments, each $R^2$ is independently selected from halo and $C_{1-6}$ alkoxy. In some embodiments, each $R^2$ is independently selected from halo and $C_{1-3}$ alkoxy. In some embodiments, each $R^2$ is independently selected from chloro and methoxy.

In some embodiments, m is 1.

In some embodiments, n is 1.

In some embodiments, the compound of Formula I is a compound of Formula II:

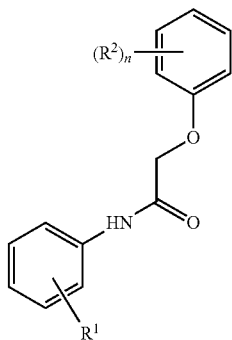

II or a pharmaceutically acceptable salt thereof.

In some embodiments the compound of Formula I is a compound of Formula III:

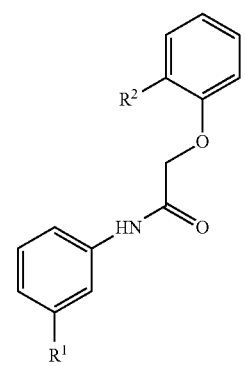

III or a pharmaceutically acceptable salt thereof.

In some embodiments, the compound of Formula I is a compound of Formula IV:

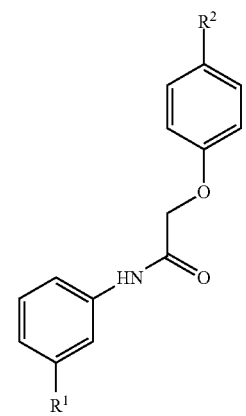

IV or a pharmaceutically acceptable salt thereof.

In some embodiments, the compound of Formula I is selected from the group consisting of:

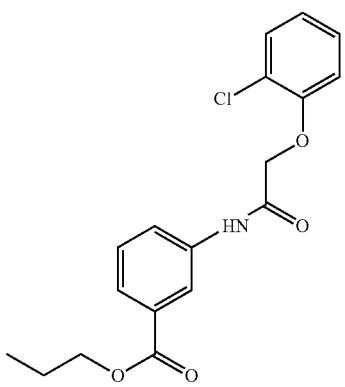 [SMILES: CCCOC(=O)c1cccc(NC(=O)COc2ccccc2Cl)c1]

,

-continued

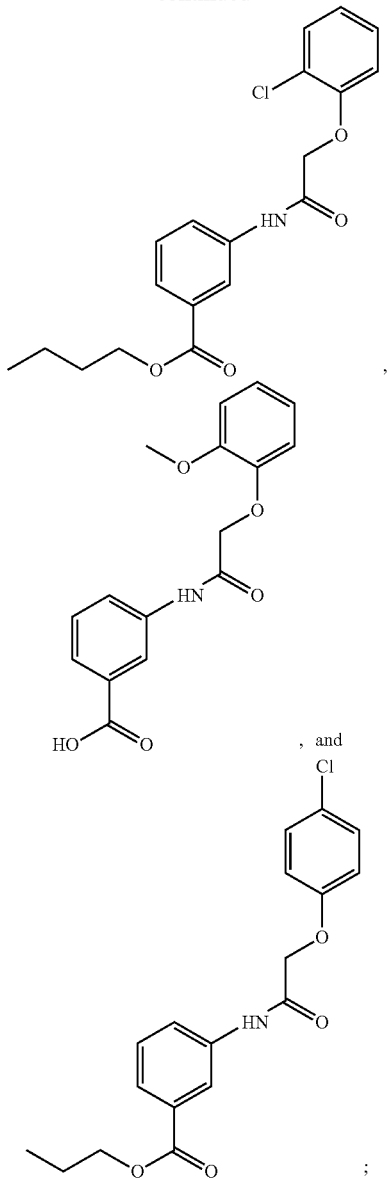

, and

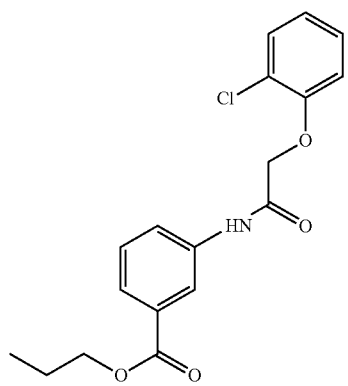 [SMILES: CCCOC(=O)c1cccc(NC(=O)COc2ccccc2Cl)c1]

or a pharmaceutically acceptable salt thereof.

In some embodiments, the compound of Formula I is:

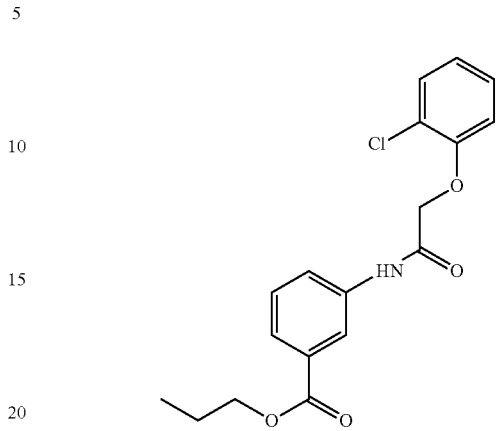

or a pharmaceutically acceptable salt thereof.

The present application further provides a method of inhibiting metastasis of triple negative breast cancer in a subject, comprising administering to the subject a compound which is:

or a pharmaceutically acceptable salt thereof.

In some embodiments, the methods provided herein further comprise administering to the subject one or more additional therapeutic agents. In some embodiments, the methods provided herein further comprise administering to the subject one or more additional chemotherapeutic agents.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIG. 6A shows SLPI regulated FoxM1 binding to the MMP2 promoter sequence in gel shift assay (EMSA). All lanes contained biotin end-labeled MMP2 duplex DNA. NP (lane 1) was a control without protein. Lanes 2 and 3 contained protein extract without and with addition of SLPI protein. Lane 4: non stimulated with SLPI protein extract. Lane 5: supershift with cells stimulated by SLPI and protein extract was incubated with FoxM1 antibodies. Arrows indicate bands shifted and supershifted by antibodies against FoxM1. Lane 6: the loss of FoxM1-specific DNA-binding in the presence of FoxM1 oligo competitor.

FIG. 6B shows SLPI increases transmigration of breast cancer cells through an endothelial layer in a transwell assay. 4T1 cells with down-regulated SLPI (SLPI shRNA) had decreased transmigration across an endothelial monolayer compared to control 4T1 cells. Error bars represent SEM; n=10, * P<0.001.

DETAILED DESCRIPTION

Figure 1A:
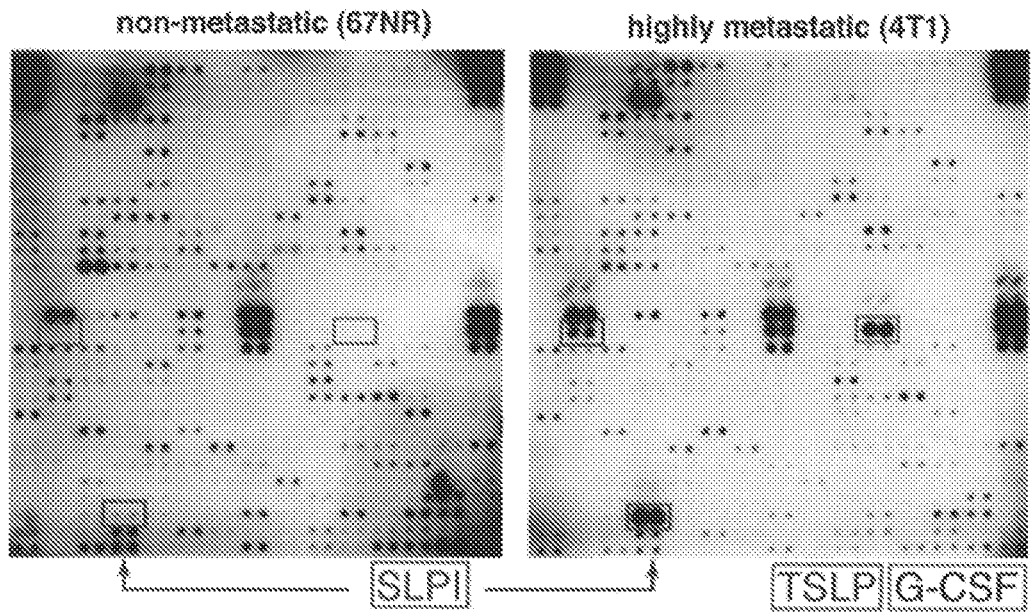
FIG. 1A shows a comparison of secreted proteins in non-metastatic (67NR) and highly metastatic (4T1) cell conditioned media using a protein array that detects 350 mouse proteins. Arrows indicate secreted proteins markedly increased in highly metastatic cells including SLPI.

Triple negative breast cancer (TNBC) is the most aggressive breast cancer subtype and has the worst prognosis, despite advancements in modern therapeutics (see e.g., Bianchini et al, *Nat. Rev. Clin. Oncol.* 2016, 13:674-690). Drug resistance, tumor invasion, and metastasis (see e.g., Sledge et al, *J. Clin. Oncol.* 2014, 32:1979-1986) contribute to the poor prognosis of TNBC, and better targeted therapies and more effective systemic treatments are needed. There are indications that breast cancer cells secrete substances that facilitate dissemination, including osteopontin, hyaluronan, metalloproteases, and integrin-binding ligands (see e.g., Chen et al, J. Proteome Res. 2008, 7:1379-1387; and Lorusso & Rüegg, *Semin. Cancer Biol.* 2012, 22:226-233). However, role these components play during invasion and metastasis of TNBC has not been confirmed, nor whether they are valid targets for inhibiting metastasis in patients (see e.g., Chaffer & Weinberg, *Science,* 2011, 331:1559-1564).

SLPI is a secreted serine protease inhibitor that serves as a protective component of the mucosa and skin (see e.g., Thompson & Ohlsson, *Proc. Natl. Acad. Sci. USA* 1986, 83:6692-6696; and Zhang et al, *J. Biol. Chem.* 2002, 277:29999-30009). SLPI has been reported to exert pleiotropic activities in multiple biological contexts. In cancer, literature has shown increased SLPI expression not only in breast cancer, but also in lung, gastric and colorectal carcinomas (see e.g., Ameshima et al, *Cancer,* 2000, 89:1448-1456; Devoogdt et al, *Proc. Natl. Acad. Sci. USA,* 2003, 100:5778-5582; and Cheng et al, *Int. J. Cancer,* 2008, 123:1787-1796). For example, patients with non-small cell lung carcinoma have higher serum SLPI levels compared to patients with small cell lung carcinoma or healthy individuals, and these levels were found to correlate with tumor stage (see e.g., Ameshima et al, *Cancer,* 2000, 89:1448-1456). However, in some cases overexpression of SLPI at the primary tumor site repressed metastases (see e.g., Cordes et al, *Int. J. Cancer,* 2011, 39:185-191; and Wang et al, *Cancer Res.* 2006, 66:3062-3070). In breast cancer, overexpression of SLPI has been associated with more aggressive, metastatic disease (see e.g., Cimino et al, *Int. J. Cancer,* 2008, 123:1327-1338; Kluger et al, *Cancer Res.,* 2005, 65:5578-5587; Sugino et al, *J. Pathol.* 2007, 212:152-160; and Sayers et al, *PLoS One,* 2014, 9:e104223), though the details of how SLPI influences tumor aggressiveness, metastatic potential, and treatment outcome remain unknown.

SLPI is known to be of significant prognostic and/or predictive value for lung, gastric, and colorectal carcinomas (see e.g., Ameshima et al, *Cancer,* 2000, 89:1448-1456; Devoogdt et al, *Proc. Natl. Acad. Sci. USA,* 2003, 100:5778-5582; Liu et al, *World J. Surg. Oncol.* 2014, 12:369; and Cheng et al, *Int. J. Cancer,* 2008, 123:1787-1796) but its role in breast cancers is somewhat less clear. In animal studies, overexpression of SLPI in implanted breast cancer cells typically lead to enhanced local growth and increased metastasis (see e.g., Kluger et al, *Cancer Res.,* 2005, 65:5578-5587; Sugino et al, *J. Pathol.* 2007, 212:152-160; and Sayers et al, *PLoS One,* 2014, 9:e104223), but the opposite effect at the primary site has also been reported (see e.g., Amiano et al, *J. Cell. Physiol,* 2013, 228:469-475). In the clinic, gene expression analysis for breast cancer patients revealed that high SLPI was associated with a shorter time to tumor relapse and shorter overall survival (see e.g., Cimino et al, *Int. J. Cancer,* 2008, 123:1327-1338), while the opposite correlation was reported for time to relapse using another dataset (see e.g., Sotiriou et al, *J. Natl. Cancer Inst.* 2006, 98:262-272); moreover, the levels and the role of SLPI expression in different breast cancer subtypes have not yet been systematically compared.

The present application discloses that highly metastatic murine 4T1 TNBC breast cancer cells produce higher levels of SLPI compared to their non-metastatic 67NR counterparts, and that SLPI level is associated with increased lung metastasis from orthotopically implanted 4T1 tumors. Applying a high-throughput screening assay to a small-molecule library, a compound that represses SLPI pharmacologically and decreases metastasis to the lung was identified. Two possible mechanisms were identified by which SLPI promote metastasis. In the first mechanism, overexpression of SLPI facilitated breast cancer cell invasion of an endothelial monolayer. In the second mechanism, SLPI physically interacts with and phosphorylates retinoblastoma (Rb) tumor suppressor protein, releasing Forkhead box transcriptional factor M1 (FoxM1) from Rb-FoxM1 complex to activate FoxM1 target genes. FoxM1 is known to be up-regulated in the majority of solid human cancers, including TNBC breast cancer, and has been implicated in invasion and metastasis (see e.g., Raychaudhuri & Park, *Cancer Res.* 71:4329-4333; Alvarez-Fernandez & Medema, *Front. Oncol.* 2013, 3:30; Saba et al, *Int. J. Breast Cancer,* 2016, 2016:9768183; and Gartel, *Cancer Res.* 2017, 77:3135-3139). Thus, the present application describes SLPI as a new target for anti-metastatic therapies, for example, in subjects having TNBC.

Accordingly, the present application provides a method of inhibiting metastasis (e.g., reducing the rate of metastasis and/or stopping metastasis) of a cancer in a subject, comprising administering to the subject a compound of Formula I:

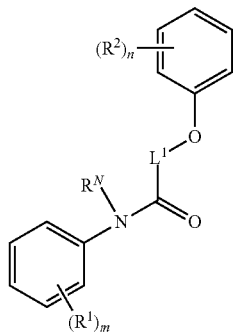

or a pharmaceutically acceptable salt thereof, wherein:

$R^N$ is selected from the group consisting of H and $C_{1-6}$ alkyl;

$L^1$ is a $C_{1-6}$ alkylene group;

each $R^1$ is independently selected from the group consisting of C(O)R and C(O)OR$^a$;

each $R^a$ is independently from the group consisting of H and $C_{1-6}$ alkyl;

each $R^2$ is independently selected from the group consisting halo, $C_{1-6}$ alkyl, $C_{1-6}$ haloalkyl, and $C_{1-6}$ alkoxy;

m is 1 or 2; and n is 1 or 2.

In some embodiments, the present application provides a method of preventing metastasis of a cancer in a subject, comprising administering to the subject a compound provided herein (e.g., a compound of any of Formulas I-IV), or a pharmaceutically acceptable salt thereof.

In some embodiments, the present application provides a method of inhibiting and/or preventing metastasis of a cancer in a subject, comprising administering to the subject a compound provided herein (e.g., a compound of any of Formulas I-IV), or a pharmaceutically acceptable salt thereof.

In some embodiments, the present application further provides a method of treating cancer in a subject, comprising administering to the subject a compound provided herein (e.g., a compound of any of Formulas I-IV), or a pharmaceutically acceptable salt thereof.

In some embodiments, the cancer is associated with abnormal levels or expression of secretory leukocyte protease inhibitor in the subject. In some embodiments, the cancer is associated with abnormal levels of secretory leukocyte protease inhibitor in the subject, compared to a normal or healthy subject (e.g., a subject without cancer). In some embodiments, the cancer is associated with increased levels of secretory leukocyte protease inhibitor in the subject, compared to a normal or healthy subject (e.g., a subject without cancer). In some embodiments, the cancer is associated with decreased levels of secretory leukocyte protease inhibitor in the subject, compared to a normal or healthy subject (e.g., a subject without cancer). In some embodiments, the cancer is associated with abnormal expression of secretory leukocyte protease inhibitor in the subject compared to a normal or healthy subject (e.g., a subject without cancer). In some embodiments, the cancer is associated with increased expression of secretory leukocyte protease inhibitor in the subject compared to a normal or healthy subject (e.g., a subject without cancer). In some embodiments, the cancer is associated with decreased expression of secretory leukocyte protease inhibitor in the subject compared to a normal or healthy subject (e.g., a subject without cancer). In some embodiments, the triple negative breast cancer is associated with abnormal retinoblastoma (Rb) tumor suppressor protein phosphorylation in the subject compared to a normal or healthy subject (e.g., a subject without cancer). In some embodiments, the triple negative breast cancer is associated with abnormal expression of Forkhead box transcriptional factor M1 (FoxM1) in the subject compared to a normal or healthy subject (e.g., a subject without cancer).

In some embodiments, the cancer is selected from breast cancer, lung cancer, gastric cancer, and colorectal cancer. In some embodiments, the cancer is breast cancer. In some embodiments, the cancer is triple negative breast cancer. In some embodiments, the cancer is lung cancer. In some embodiments, the cancer is non-small cell lung cancer. In some embodiments, the cancer is gastric cancer. In some embodiments, the cancer is colorectal cancer.

In some embodiments, the present application further provides a method of inhibiting secretion (e.g., reducing the rate of secretion and/or stopping secretion) of secretory leukocyte protease inhibitor in a cell, comprising contacting the cell with a compound provided herein (e.g., a compound of any of Formulas I-IV), or a pharmaceutically acceptable salt thereof. In some embodiments, the method is an in vitro method. In some embodiments, the method is an in vivo method.

The present application further provides a method of inhibiting secretion (e.g., reducing the rate of secretion and/or stopping secretion) of secretory leukocyte protease inhibitor in a subject (e.g., a subject in need thereof), comprising administering to the subject a compound provided herein (e.g., a compound of any of Formulas I-IV), or a pharmaceutically acceptable salt thereof.

In some embodiments, the present application further provides a method of inhibiting expression (e.g., reducing expression and/or stopping expression) of secretory leukocyte protease inhibitor in a cell, comprising contacting the cell with a compound provided herein (e.g., a compound of any of Formulas I-IV), or a pharmaceutically acceptable salt thereof. In some embodiments, the method is an in vitro method. In some embodiments, the method is an in vivo method.

In some embodiments, the present application further provides a method of inhibiting expression (e.g., reducing expression and/or stopping expression) of secretory leukocyte protease inhibitor in a subject (e.g., a subject in need thereof), comprising administering to the subject a compound provided herein (e.g., a compound of any of Formulas I-IV), or a pharmaceutically acceptable salt thereof.

In some embodiments, the present application further provides a method of inhibiting retinoblastoma (Rb) tumor suppressor protein phosphorylation (e.g., reducing the rate of phosphorylation and/or stopping phosphorylation) in a cell, comprising contacting the cell with a compound provided herein (e.g., a compound of any of Formulas I-IV), or a pharmaceutically acceptable salt thereof. In some embodiments, the method is an in vitro method. In some embodiments, the method is an in vivo method.

In some embodiments, the present application further provides a method of inhibiting retinoblastoma (Rb) tumor suppressor protein phosphorylation (e.g., reducing the rate of phosphorylation and/or stopping phosphorylation) in a subject (e.g., a subject in need thereof), comprising administering to the subject a compound provided herein (e.g., a compound of any of Formulas I-IV), or a pharmaceutically acceptable salt thereof.

In some embodiments, the method of inhibiting retinoblastoma (Rb) tumor suppressor protein phosphorylation comprises inhibiting SLPI activated retinoblastoma (Rb) tumor suppressor protein phosphorylation.

In some embodiments, the present application further provides a method of inhibiting expression (e.g., reducing expression and/or stopping expression) of Forkhead box transcriptional factor M1 (FoxM1) in a cell, comprising contacting the cell with a compound provided herein (e.g., a compound of any of Formulas I-IV), or a pharmaceutically acceptable salt thereof. In some embodiments, the method is an in vitro method. In some embodiments, the method is an in vivo method.

The present application further provides a method of inhibiting expression (e.g., reducing expression and/or stopping expression) of Forkhead box transcriptional factor M1 (FoxM1) in a subject (e.g., a subject in need thereof), comprising administering to the subject a compound provided herein (e.g., a compound of any of Formulas I-IV), or a pharmaceutically acceptable salt thereof.

The present application further provides a method of inhibiting activation (e.g., reducing the rate of activation and/or stopping activation) of Forkhead box transcriptional factor M1 (FoxM1) signaling in a subject (e.g., a subject in need thereof), comprising administering to the subject a compound provided herein (e.g., a compound of any of Formulas I-IV), or a pharmaceutically acceptable salt thereof.

In some embodiments, $R^N$ is selected from the group consisting of H and $C_{1-3}$ alkyl. In some embodiments, $R^N$ is H.

In some embodiments, $L^1$ is a $C_{1-3}$ alkylene group. In some embodiments, $L^1$ is methylene.

In some embodiments, each $R^1$ is $C(O)OR^a$. In some embodiments, each $R^a$ is independently selected from the group consisting of H and $C_{3-6}$ alkyl. In some embodiments, each $R^a$ is independently selected from the group consisting of H, propyl, and butyl. In some embodiments, each $R^a$ is independently selected from the group consisting of H, n-propyl, and n-butyl. In some embodiments, each $R^1$ is selected from $C(O)OH$, $C(O)CH_2CH_2CH_3$, and $C(O)CH_2CH_2CH_2CH_3$.

In some embodiments, each $R^2$ is independently selected from halo and $C_{1-6}$ alkoxy. In some embodiments, each $R^2$ is independently selected from halo and $C_{1-3}$ alkoxy. In some embodiments, each $R^2$ is independently selected from chloro and methoxy. In some embodiments, each $R^2$ is chloro. In some embodiments, each $R^2$ is methoxy.

In some embodiments, m is 1. In some embodiments, m is 2.

In some embodiments, n is 1. In some embodiments, n is 2.

In some embodiments, m is 1 and n is 1. In some embodiments, m is 1 and n is 2. In some embodiments, m is 2 and n is 1. In some embodiments, m is 2 and n is 2.

In some embodiments, the compound of Formula I is a compound of Formula II:

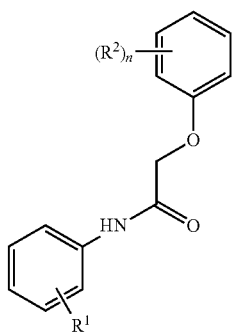

II or a pharmaceutically acceptable salt thereof, wherein variables $R^1$, $R^2$, and n are defined according to the definitions provided herein for compounds of Formula I.

In some embodiments, the compound of Formula I is a compound of Formula III:

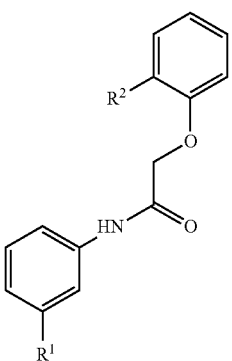

III or a pharmaceutically acceptable salt thereof, wherein variables $R^1$ and $R^2$ are defined according to the definitions provided herein for compounds of Formula I.

In some embodiments, the compound of Formula I is a compound of Formula IV:

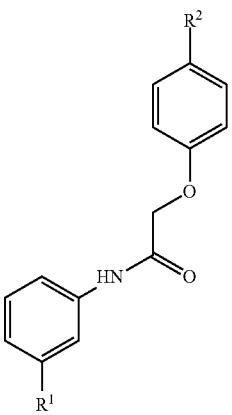

IV or a pharmaceutically acceptable salt thereof, wherein variables $R^1$ and $R^2$ are defined according to the definitions provided herein for compounds of Formula I.

In some embodiments, the compound of Formula I is selected from the group consisting of:

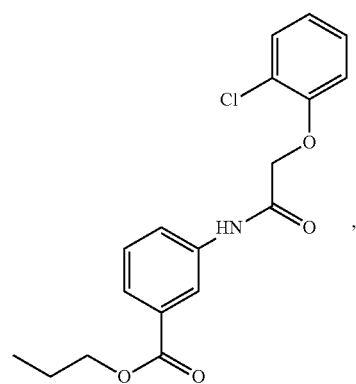

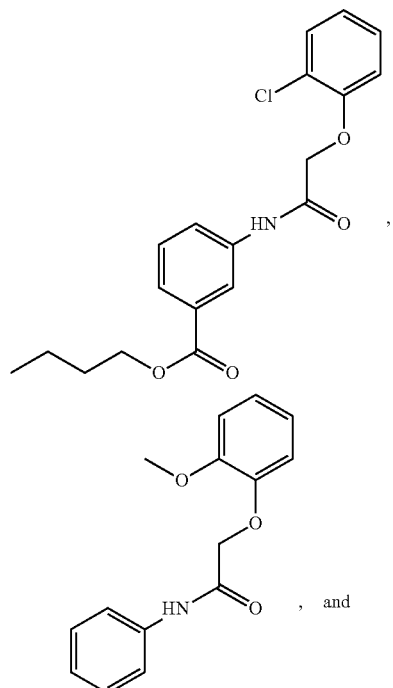

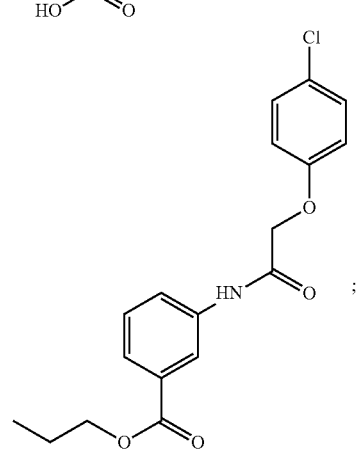

or a pharmaceutically acceptable salt thereof.

In some embodiments, the compound of Formula I is:

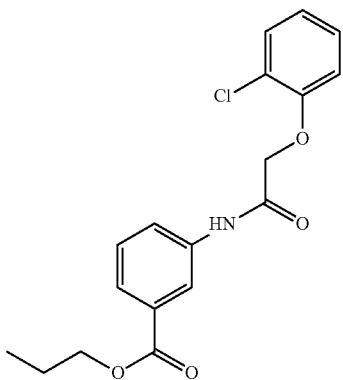 [SMILES: CCCOC(=O)c1cccc(NC(=O)COc2ccccc2Cl)c1]

or a pharmaceutically acceptable salt thereof.

In some embodiments, the present application further provides a method of inhibiting metastasis of triple negative breast cancer in a subject, comprising administering to the subject a compound which is:

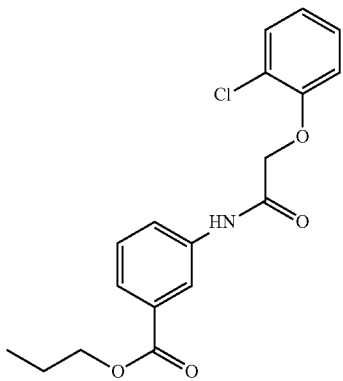 [SMILES: CCCOC(=O)c1cccc(NC(=O)COc2ccccc2Cl)c1]

or a pharmaceutically acceptable salt thereof. In some embodiments, the triple negative breast cancer is associated with abnormal levels or expression of secretory leukocyte protease inhibitor in the subject. In some embodiments, the triple negative breast cancer is associated with abnormal levels of secretory leukocyte protease inhibitor in the subject, compared to a normal or healthy subject (e.g., a subject without triple negative breast cancer). In some embodiments, the triple negative breast cancer is associated with increased levels of secretory leukocyte protease inhibitor in the subject, compared to a normal or healthy subject (e.g., a subject without triple negative breast cancer). In some embodiments, the triple negative breast cancer is associated with decreased levels of secretory leukocyte protease inhibitor in the subject, compared to a normal or healthy subject (e.g., a subject without triple negative breast cancer). In some embodiments, the triple negative breast cancer is associated with abnormal expression of secretory leukocyte protease inhibitor in the subject compared to a normal or healthy subject (e.g., a subject without triple negative breast cancer). In some embodiments, the triple negative breast cancer is associated with increased expression of secretory leukocyte protease inhibitor in the subject compared to a normal or healthy subject (e.g., a subject without triple negative breast cancer). In some embodiments, the triple negative breast cancer is associated with decreased expression of secretory leukocyte protease inhibitor in the subject compared to a normal or healthy subject (e.g., a subject without triple negative breast cancer). In some embodiments, the triple negative breast cancer is associated with abnormal retinoblastoma (Rb) tumor suppressor protein phosphorylation in the subject compared to a normal or healthy subject (e.g., a subject without triple negative breast cancer). In some embodiments, the triple negative breast cancer is associated with abnormal expression of Forkhead box transcriptional factor M1 (FoxM1) in the subject compared to a normal or healthy subject (e.g., a subject without triple negative breast cancer).

As used herein, the term "subject," refers to any animal, including mammals. Example subjects include, but are not limited to, mice, rats, rabbits, dogs, cats, swine, cattle, sheep, horses, primates, and humans. In some embodiments, the subject is a human. In some embodiments, the method comprises administering to the subject a therapeutically effective amount of a compound provided herein (e.g., a compound of any of Formulas I-IV), or a pharmaceutically acceptable salt thereof.

The compounds provided herein can be prepared, for example, according to one or more processes using a broad repertoire of synthetic organic reactions. Suitable synthetic methods of starting materials, intermediates, and products may be identified by reference to the literature, including reference sources such as: Advances in Heterocyclic Chemistry, Vols. 1-107 (Elsevier, 1963-2012); *Journal of Heterocyclic Chemistry* Vols. 1-49 (*Journal of Heterocyclic Chemistry*, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "C-m" indicates a range which includes the endpoints, wherein n and m are integers and indicate the number of carbons. Examples include $C_{1-4}$, $C_{1-6}$, and the like.

As used herein, the term "$C_{n-m}$ alkylene", employed alone or in combination with other terms, refers to a divalent alkyl linking group having n to m carbons. Examples of alkylene groups include, but are not limited to, methylene, ethan-1,2-diyl, propan-1,3-diyl, propan-1,2-diyl, and the like. In some embodiments, the alkylene moiety contains 1 to 6, 1 to 3, or 1 to 2 carbon atoms.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "halo" refers to fluoro, chloro, bromo, or iodo. In some embodiments, the halo is fluoro, chloro, or bromo. In some embodiments, the halo is chloro.

As used herein, the term "$C_{n-m}$ haloalkyl", employed alone or in combination with other terms, refers to an alkyl group having from one halogen atom to $2s+1$ halogen atoms which may be the same or different, where "s" is the number of carbon atoms in the alkyl group, wherein the alkyl group has n to m carbon atoms. In some embodiments, the haloalkyl group contains from 1 to 6 carbon atoms, from 1 to 4 carbon atoms, from 1 to 3 carbon atoms, or 1 to 2 carbon atoms.

As used herein, the term "$C_{n-m}$ alkoxy", employed alone or in combination with other terms, refers to a group of having the formula —O($C_{n-m}$ alkyl), wherein the alkyl group has n to m carbon atoms. In some embodiments, the alkoxy group contains from 1 to 6 carbon atoms, from 1 to 4 carbon atoms, from 1 to 3 carbon atoms, or 1 to 2 carbon atoms.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g., hydrates and solvates) or can be isolated.

In some embodiments, preparation or isolation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds and salts provided herein are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in Remington's Pharmaceutical Sciences, 17th ed., Mack Publishing Company, Easton, Pa., 1985, p. 1418 and *Journal of Pharmaceutical Science*, 66, 2 (1977). Conventional methods for preparing salt forms are described, for example, in *Handbook of Pharmaceutical Salts: Properties, Selection, and Use*, Wiley-VC H, 2002.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

Combination Therapies

One or more additional therapeutic agents such as, for example, anti-inflammatory agents, chemotherapeutic agents, and anesthetics (e.g., for use in combination with a surgical procedure), or other agents useful for the treatment of cancer or inhibition of cancer metastasis can be used in combination with the compounds and salts provided herein.

Example anti-inflammatory agents include, but are not limited to, aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

Exemplary chemotherapeutic agents include, but are not limited to, cytostatic agents, cisplatin, doxorubicin, taxol, etoposide, irinotecan, topotecan, paclitaxel, docetaxel, epothilones, tamoxifen, 5-fluorouracil, methotrexate, temozolomide, cyclophosphamide, tipifarnib, gefitinib, erlotinib (e.g., erlotinib hydrochloride), imatinib mesylate, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, pentostatin, vinblastine, vincristine, vindesine, bleomycin, dactinomycin, daunorubicin, epirubicin, idarubicin, mithramycin, deoxycoformycin, teniposide, fluoxymesterone, dromostanolone propionate, testolactone, megestrol acetate, methylprednisolone, methyltestosterone, aminoglutethimide, estramustine, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, porfimer, erbitux, thiotepa, altretamine, trastuzumab, fulvestrant, exemestane, rituximab, alemtuzumab, clofarabine, cladribine, aphidicolin, sunitinib, dasatinib, tezacitabine, triapine, didox, trimidox, amidox, bendamustine, ofatumumab, and idelalisib.

Exemplary anesthetics include, but are not limited, to local anesthetics (e.g., lidocaine, procain, ropivacaine) and general anesthetics (e.g., desflurane, enflurane, halothane, isoflurane, methoxyflurane, nitrous oxide, sevoflurane, mmobarbital, methohexital, thiamylal, thiopental, diazepam, lorazepam, midazolam, etomidate, ketamine, propofol, alfentanil, fentanyl, remifentanil, buprenorphine, butorphanol, hydromorphone levorphanol, meperidine, methadone, morphine, nalbuphine, oxymorphone, pentazocine).

In some embodiments, the additional therapeutic agent is administered simultaneously with a compound or salt provided herein. In some embodiments, the additional therapeutic agent is administered after administration of the compound or salt provided herein. In some embodiments, the additional therapeutic agent is administered prior to administration of the compound or salt provided herein. In some embodiments, the compound or salt provided herein is administered during a surgical procedure. In some embodiments, the compound or salt provided herein is administered in combination with an additional therapeutic agent during a surgical procedure.

Pharmaceutical Formulations

When employed as pharmaceuticals, the compounds and salts provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. In some embodiments, the compounds, salts, and pharmaceutical compositions provided herein are suitable for parenteral administration. In some embodiments, the compounds, salts, and pharmaceutical compositions provided herein are suitable for intravenous administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided are pharmaceutical compositions which contain, as the active ingredient, a compound provided herein, or a pharmaceutically acceptable salt thereof, in combination with one or more pharmaceutically acceptable carriers (e.g., excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active ingredient can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

EXAMPLES

Human triple-negative MDA-MB-231, LS174T, HEK293T and MCF-7 and MDA-MB 468 cell lines were obtained from the ATCC collection. MDA-MB-468 cells stably expressing luciferase plasmid driven by the SLPI promoter were used for high-throughput screening. To generate SLPI overexpressing cells, cancer cells were infected with pBabe-SLPI retroviruses containing the LTR promoter and puromycin resistant genes. The SLPI knockdown 4T1 cell line was established by lentiviral infection of 4T1 cells. Lentiviral particles were produced by transfecting 293T cells with two different shRNA clones that targeted SLPI (MISSION shRNA Sigma) and viral packages (VSVG, psPAX2) using FuGENE reagent (Promega, US). SLPI down-regulation was confirmed by using both q-PCR and ELISA.

Data from the Examples are expressed as mean SEM For statistical analysis, JMP Statistical analysis software was used (SAS Institute, NC). Two-tailed t tests were used to compare data between two groups. A p-value less than 0.05 was considered to be statistically significant Example 1. Detection of the Expression Levels of Secreted Proteins Mouse and human antibody arrays (RayBiotech, Inc, US) were used for detection of proteins in cell culture supernatant. The expression levels of 308 mouse and 507 human target proteins were simultaneously detected, including cytokines, chemokines and other secreted proteins. The biotin-labeled samples were added onto array, incubated with HRP-streptavidin, and subsequently visualized by chemiluminescence according to manufacturer protocol.

To assess if highly metastatic murine breast cancer cells (4T1) secrete different factors from those secreted by strain-matched but non-metastatic cells (67NR), conditioned media from both cell lines was screened using a mouse-specific antibody array. Three secreted proteins were identified that were selectively and significantly increased in 4T1 cells: SLPI, TSLP (thymic stromal lymphopoietin), and G-CSF (granulocyte colony-stimulating factor) (FIG. 1A). To determine if the difference in SLPI secretion was unique to these TNBCs, conditioned media from a highly metastatic colorectal cancer line Lim6 and its poorly metastatic parental line LS174T were also analyzed (see e.g., Bresalier et al, *J. Clin. Invest.* 1991, 87:1037-1045) using a similar human antibody array for detection of 500 secreted proteins. Only four secreted proteins; Glypican 3, SLPI, MIP2, and TIMP-1, were up-regulated in highly metastatic Lim6 compared to non-metastatic LSI74T conditioned media. SPLI was the only secreted factor increased in metastatic variants of both breast and colorectal cancer cells.

Figure 1B:
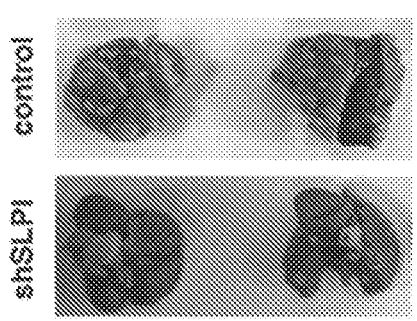
FIG. 1B shows that down-regulation of SLPI using shRNA in 4T1 cells inhibits lung metastases. Mice were implanted with control or SLPI-shRNA 4T1 tumors orthotopically and the lungs were examined for metastases (whitish nodules) 21 days after primary tumor resection. Lungs from mice pre-implanted with SLPI-shRNA tumors exhibited fewer metastases (shSLPI).
Figure 1C:
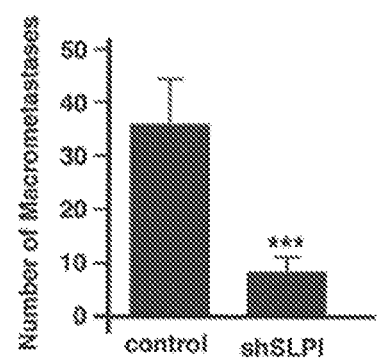
FIG. 1C shows the number of macrometastases (colonies at least 0.5 mm in diameter) per mouse was significantly less in the mice bearing the SLPI-shRNA tumors (n=7 for each group, *p=0.004).

To investigate which, if any, of the three proteins secreted by the metastatic breast cancer cells (i.e., SLPI, TSLP, and G-CSF) have a functional role in tumor growth and metastasis, lentivirally-transduced shRNA was used to stably inhibit translation of SLPI, TSLP, or G-CSF in 4T1 cells. The parental or modified 4T1 cells were injected into the mammary fat pad of BALB/c mice. When the implanted tumors reached approximately 6 mm in diameter, the tumors were resected and the numbers of lung metastases were assessed 21 days later. It was found that down-regulation of G-CSF and TLSP had no significant effect on metastasis, but mice bearing 4T1 SLPI shRNA tumors (with SLPI expression ~10% of control cell levels measured in 4T1 cells) had significantly fewer lung metastases compared to the control group (see FIGS. 1B-1C). Without being bound by theory, these results suggested that high expression of SLPI in such breast cancer cells promotes lung metastasis.

Example 2. High-Throughput Screening (HTS)

After establishing that SLPI is a valid target for inhibiting TNBC metastasis, small molecules for use in inhibiting SLPI pharmacologically were screened. Human TNBC cell line MDA-MB-468 with a Luciferase plasmid driven by the SLPI promoter was used to perform high-throughput screening of a small-molecule library of 60,000 chemically-diverse compounds. Compounds (5 µM) were diluted in 100% DMSO, and spotted per well to 384-well plates using a Multimek 96/384 Channel Automated Pipetter. A cell-based readout system was used for compound selection. MDA-MB-468 cells stably expressing luciferase plasmid driven by the 251 bp SLPI promoter were used for high-throughput screening. For cell-based screening, a cell density of 10,000 breast cancer cells/well was selected to produce the most prominent signal. MDA-MB-468 cells were treated with 5 µM of compound for 24 hours. Selected compounds were also analyzed with 90% of SLPI repression. Toxic compounds were removed from selection groups by analyzing treatment effects on normal human umbilical vein endothelial cells (HUVEC).

Figure 3A:
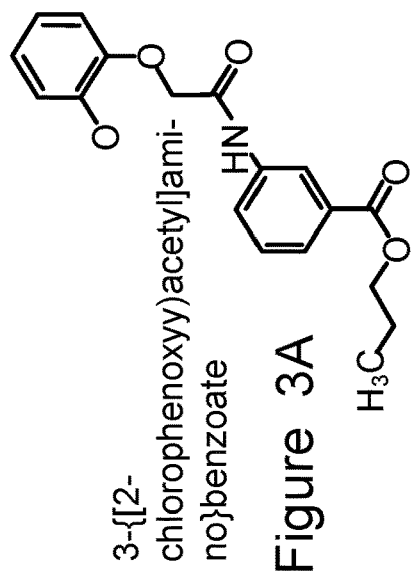
FIG. 3A shows the molecular structure of compound C74 (propyl 3-(2-(2-chlorophenoxy)acetamido)benzoate).
Figure 3B:
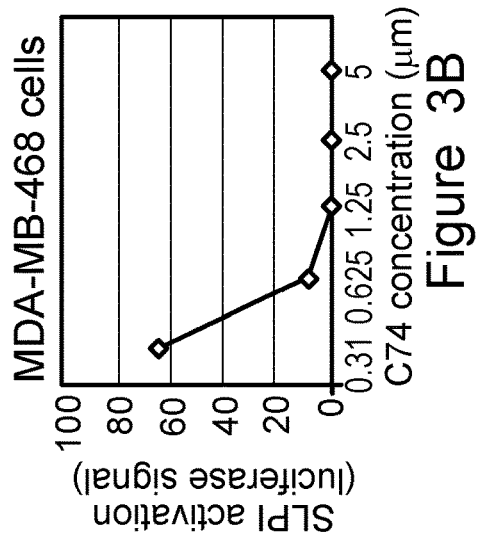
FIG. 3B shows C74 inhibition of SLPI expression by MDA-MB-468 cells. Cells were treated with C74 (0.31 to 5 M) for 24 hours and SLPI expression was quantified using luciferase activity driven by the SLPI promoter.
Figure 3C:
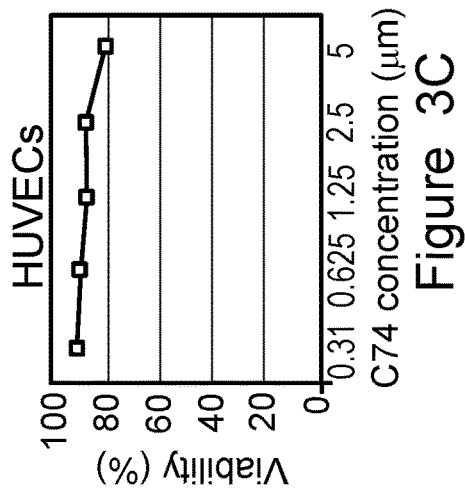
FIG. 3C shows viability of HUVEC, MDA-MB-468, and 4T1 cancer cells treated with C74 for 24 hours evaluated using a MTT assay.

The objective of the HTS was to identify new biologically active small molecules that were able to reduce SLPI expression in cancer cells by at least 90% without apparent cytotoxicity. 176 compounds were selected that produced ≥90% Luciferase inhibition at a concentration of 5 µM. Dose dependence of SLPI repression was confirmed for candidate compounds at five different concentrations (0.31 µM, 0.625 µM, 1.25 µM, 2.5 µM, and 5 µM). FIG. 3A demonstrates the results of such an experiment for a representative compound, (propyl 3-{[(2-chlorophenoxy)acetyl]amino}benzoate; i.e., Compound C74). 94 of the 176 compounds were selected for having no effect on cell viability and proliferation in a MTT assay. The compound C74 exhibited no toxic effect on MDA-MB-468 and 4T1 cancer cells as well as to normal HUVEC (see FIG. 3C).

Example 3. Assessment of Spontaneous Lung Metastases

Figure 3D:
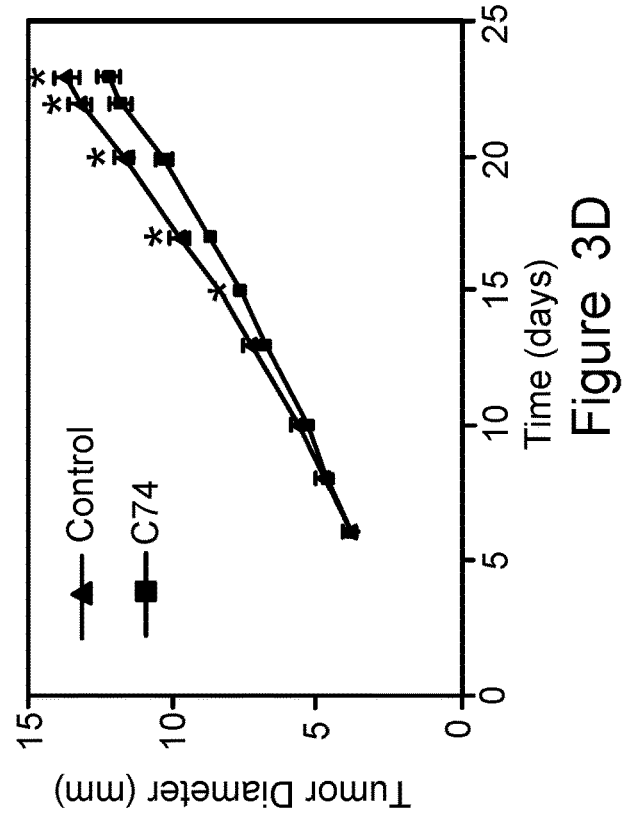
FIGS. 3D-3E show that anti-SLPI compound C74 suppressed tumor growth and metastasis of 4T1 TNBC in mice. 4T1 cells were injected in the mammary fat pad of female BALB/c mice and the mice were treated with C74 (25 mg/kg) daily for 12 days (from day 6 to day 17) via intraperitoneal injection (FIG. 3D). Error bars in FIG. 3D represent SEM; n=8 mice/group, * P<0.05. Quantification of the numbers of large (>1 mm, black bar) and total lung metastases (white bar) observed after harvesting lungs on day 23 are shown in FIG. 3E. Error bars in FIG. 3E represent SEM; n=8 mice/group, * P<0.05.

Next, we tested whether treatment with the selected SLPI inhibitor C74 would decrease metastasis in vivo. Parental and modified 4T1 cells were injected into the third mammary fat pad of 8-week-old female BALB/C mice, $10^5$ cells in 20 µL of HANKS per injection. The growing tumors were then either resected at a certain size or left as is. In the latter case, the mice were treated daily with intraperitoneal (i.p.) delivery of 20 mg/kg of the selected compound suppressing SLPI (or vehicle), for 12 consecutive days starting from day 6 after tumor implantation, when tumors were ~3.8 mm in diameter on average (see FIG. 3D). The mice were sacrificed either on day 21 post primary tumor resection or 17 days after compound treatment initiation. The lungs were removed and placed in Bouin's solution (Sigma). A few days later, the lung surface was examined under a stereomicroscope and the number and size of metastases were evaluated.

During the 12-day treatment with compound C74, there was a small, progressive inhibition of primary tumor growth, which resulted in a statistically significant difference in tumor diameters between the groups. This difference was sustained after therapy stopped. C74 did not cause changes in mouse weight, appearance, or behavior.

Figure 3E:
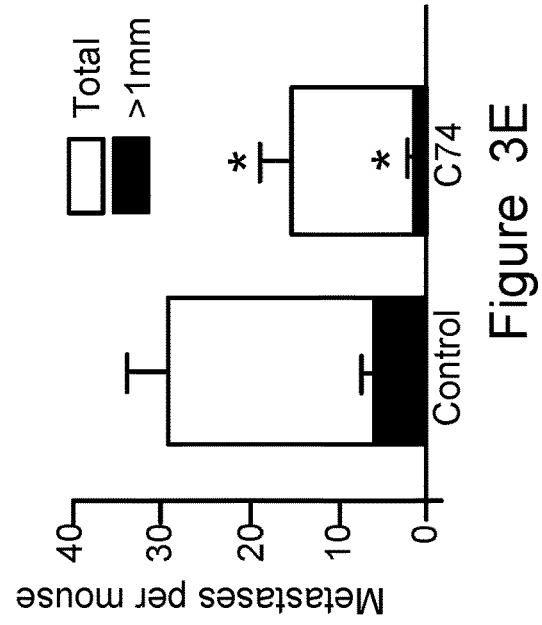

Metastases in the lungs were evaluated after sacrifice of the mice on day 23, as shown in FIG. 3E. The total number of metastases in the treatment group decreased by 50%, and the metastatic colonies were much smaller.

Example 4. Patient Survival Analysis

The Kaplan-Meier Plotter (see e.g., Győrffy et al, *PLoS One*, 2013, 8:e82241) was used to compute Kaplan-Meier plots for SLPI in basal intrinsic subtype and for all breast cancer patients. A database of 2014 patients was analyzed and correlated Affymetrix microarray results for SLPI (measured in patient tumor samples) with associated survival information, with a mean follow-up of 69 months. The Plotter automatically determined the median-based cut-off used to split the patients into "high SLPI" and "low SLPI" expression categories. The probe 203021_at was selected for SLPI. Analysis was performed using default parameters and the exclusion of outlier arrays from the array quality control tab.

Figure 2A:
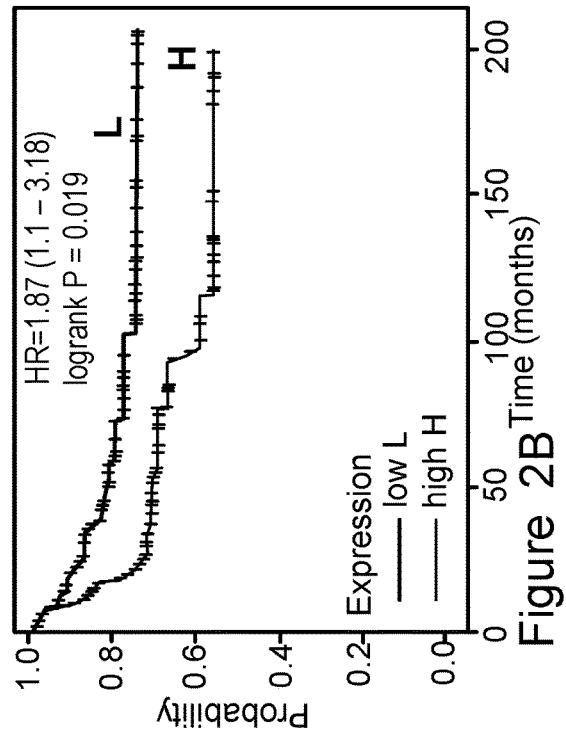
FIG. 2A shows overall survival (n=219) in basal breast cancer patients with low (black trace) or high (red trace) levels of SLPI expression based on the median value.
Figure 2B:
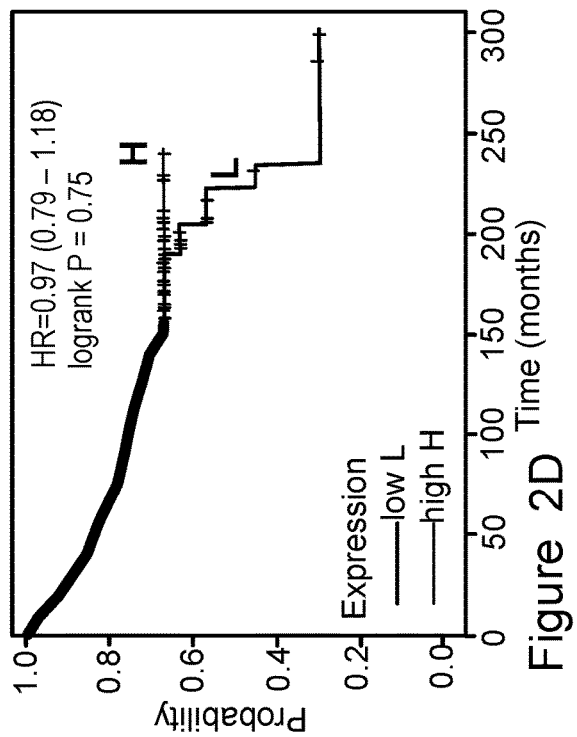
FIG. 2B shows distant metastasis-free survival (n=226) in basal breast cancer patients with low (black trace) or high (red trace) levels of SLPI expression based on the median value.
Figure 2C:
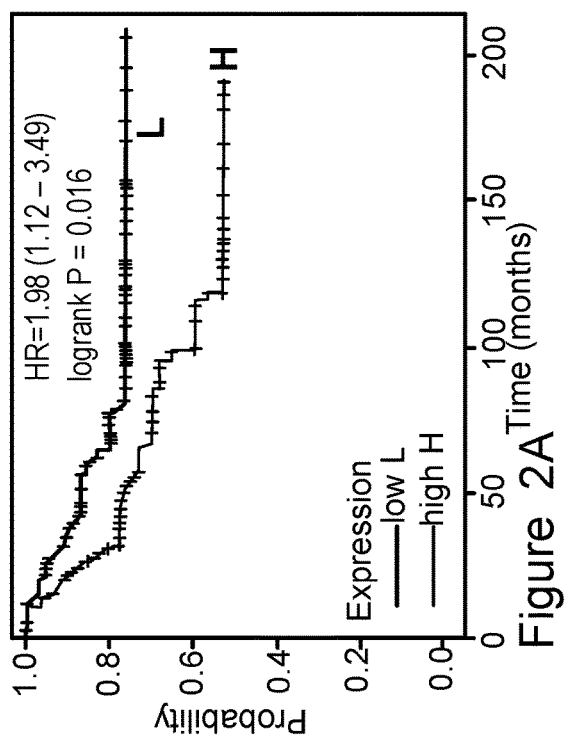
FIGS. 2C-2D show overall survival (FIG. 2C; n=1117) and distant metastasis-free survival (FIG. 2D; n=1609) in all subgroups of breast cancer patients with low or high SLPI expression. HR=hazard ratio.
Figure 2D:
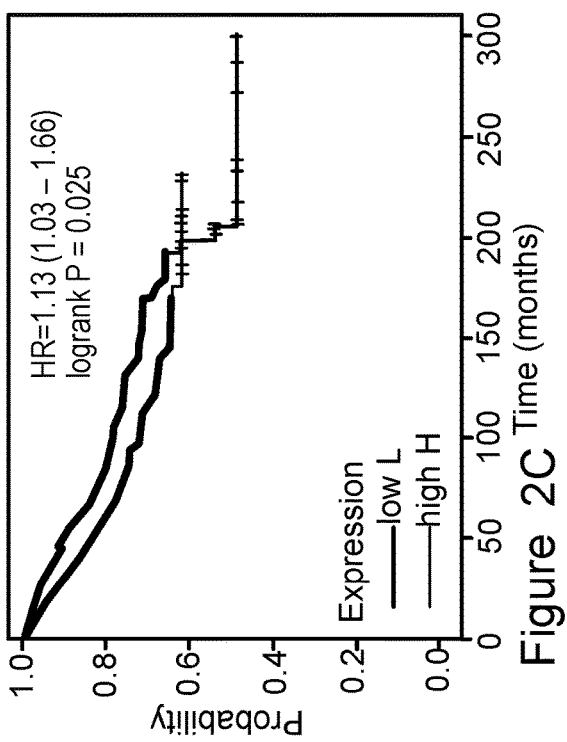

Both distant metastasis-free survival and overall survival were found to be significantly worse in the Basal/TNBC subtype of breast cancer patients with higher SLPI expression in tumor samples, as shown in FIGS. 2A-2B. Analysis that included all breast cancer patients regardless of their intrinsic subtype also revealed a slightly better overall survival of patients with lower SLPI levels, but there was no significant difference in their distant metastasis-free survival, as shown in FIGS. 2C-2D. These clinical data are consistent with experimental results and support the hypothesis that SLPI regulates metastasis in TNBCs.

Example 5. Western Blotting and Immunoprecipitation

Lysates from 293T, MDA-MB-231, MCF7 and 4T1 cells were prepared in lysis buffer containing Tris-HCl 50 mM/pH 7.4; NaCl 150 mM; NP-40 1%; SDS 0.1%; Na-deoxycholate 0.5%; EDTA 1 mM; plus 1% phosphatase inhibitor cocktails I and II (Sigma-Aldrich, US), and 1% protease inhibitor cocktail (Roche). Equal amounts of protein (50 µg/sample) were resolved by SDS-PAGE, transferred onto nitrocellulose membranes, and immunoblotted using the following primary antibodies: anti-SLPI, anti-RB (Cell Signaling and Santa Cruz Biotechnology, US), anti-SOD2, Aurora kinase, cyclin B1 and anti-β-catenin (Cell Signaling Technology). For co-IP assays, lysates were pre-cleared with IgG, and incubated with anti-SLPI, anti-RB or control IgG antibodies linked to Sepharose-A beads. Protein complexes were dissociated from beads and separated by SDS-PAGE. Immunodetection was performed by incubation with HRP-conjugated species-specific antibodies, followed by chemiluminescence detection (Perkin Elmer, US).

Figure 4A:
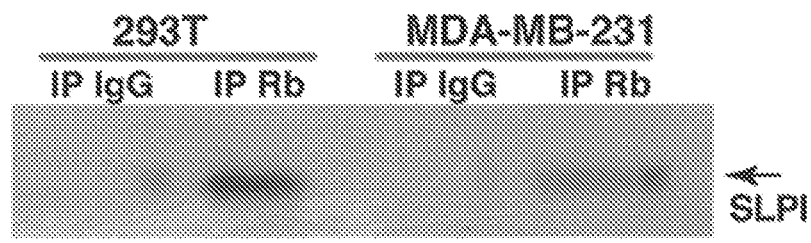
FIG. 4A-4B show co-immunoprecipitation of SLPI and Rb. Total cell lysates from two different cell lines (MDA-MB-231 and HEK293T) were immunoprecipitated and analyzed by immunoblotting with antibodies against SLPI and Rb. Irrelevant isotype-matched IgG antibody was used as a control.
Figure 4B:
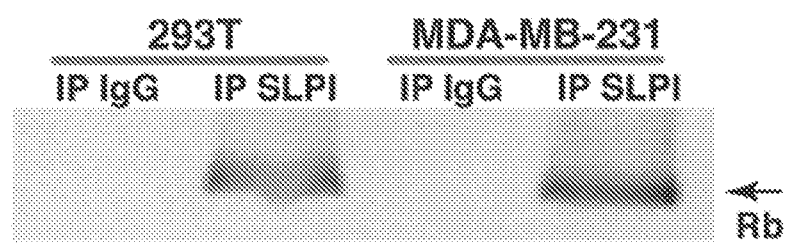

SLPI promotes migration, invasion, and metastasis of gastric cancer cells by increasing expression of MMP-2 and MMP-9 genes (see e.g., Choi et al, Int. J. Mol. Med. 2011, 28:527-534), and the latter could have been targeted by transcriptional factor FoxM1 (see e.g., Dai et al, *Oncogene*, 2007, 26:6212-6219; Uddin et al, *Am. J. Pathol.* 2011, 178:537-547; and Jiang et al, *Ups. J. Med. Sci.* 2014, 119:324-332)). Furthermore, activation of FoxM1 signaling is generally associated with cancer cellular proliferation, invasion, and metastasis (see e.g., Raychaudhuri & Park, *Cancer Res.* 71:4329-4333; and Saba et al, *Int. J. Breast Cancer*, 2017, 77:3135-3139), and FoxM1 is overexpressed in basal/TNBC (see e.g., Saba et al, *Int. J. Breast Cancer*, 2017, 77:3135-3139). Without being bound by theory, it is hypothesized that SLPI either directly targets FoxM1, or affects proteins that physically interact with FoxM1 (see e.g., Kalinichenko et al, *Genes Dev.* 2004, 18:830-850). To test this hypothesis, co-immunoprecipitation experiments were performed with FoxM1 and its binding partners including tumor suppressor Rb (see e.g., Raychaudhuri & Park, *Cancer Res.* 71:4329-4333; and Saba et al, *Int. J. Breast Cancer*, 2017, 77:3135-3139; and Wierstra & Alves, *Biol. Chem.* 2006, 387:949-962). To determine whether SLPI interacts with Rb, protein extracts from two different breast cancer cell lines were used. Antibody against Rb was used to precipitate Rb complexes and Western blotting with anti-SLPI antibody monitored the presence of SLPI protein in precipitates. SLPI co-immunoprecipitated with Rb, but not with normal rabbit immunoglobulin (IgG), indicating that there is a physical association between these two proteins, as shown in FIG. 4A. This interaction was further confirmed by the reverse experiment, in which anti-SLPI antibody was used for immunoprecipitation and anti-Rb antibody was used for detection, as shown in FIG. 4B.

Figure 4C:
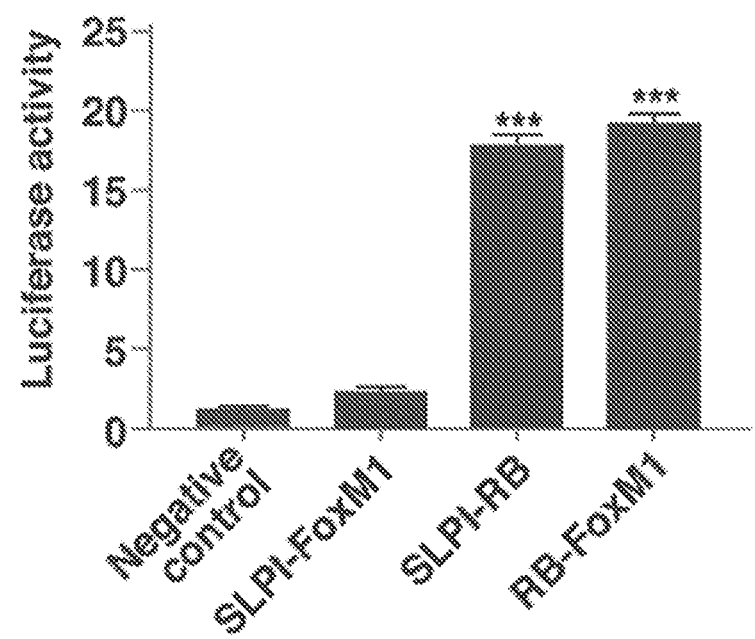
FIG. 4C shows interaction between SLPI and Rb assessed by mammalian two-hybrid system. Rb was cloned into pBIND, and SLPI and FoxM1 into pACT vectors to generate fusion proteins. Forty-eight hours after transfection, the cells were lysed and the amount of luciferases were quantitated using the Dual-Luciferase Reporter Assay System. pACT-FoxM1 and pBIND-Rb were used as a positive control for established physical interaction. Error bars represent SEM; n=3, * P<0.01.

For further verification of this interaction, a standard mammalian two-hybrid approach was used. The two genes encoding two of the three potentially interactive proteins of interest (Rb, SLPI and FoxM1) were cloned into pBIND and pACT vectors to generate fusion proteins with the DNA-binding domain of GAL4 and the activation domain of VP16. HEK293T cells were transiently transfected with a pG5luc luciferase reporter plasmid, pGAL4 and pVP16 fusion constructs. After two days, the transfected cells were lysed and the levels of luciferase were quantitated. Interaction between the two test proteins results in an increase in luciferase expression over the negative controls that included pBIND and pACT vectors. The pairs of fusion proteins GAL4-Rb plus VP16-SLPI induced activation of the reporter construct about 7 times more than the negative controls, as shown in FIG. 4C. Thus results from the mammalian two-hybrid system indicated that SLPI protein physically interacted with Rb tumor suppressor but not FoxM1, and also confirmed the known interaction of Rb and FoxM1 proteins.

Example 6. Immunohistochemistry and Imaging

Breast cancer cells were grown in 8 wells slide chambers coated with 0.1% gelatin. Once the cells form a confluent monolayer, the cells were fixed and stained for SLPI with SLPI antibodies (Sigma). Stained cells were imaged using Olympus IX81 scanning confocal microscope with 60×1.35NA oil immersion UplanSApo lens.

Figure 4D:
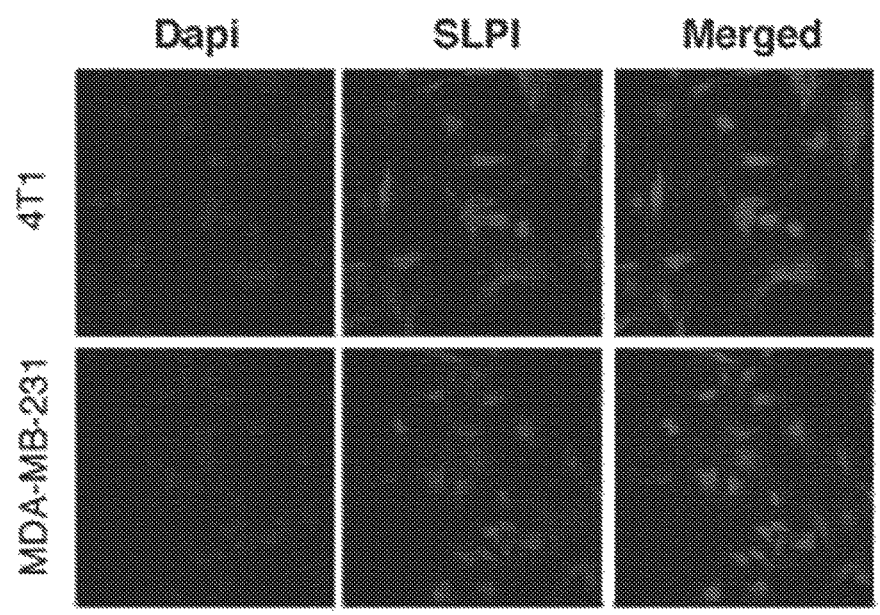
FIG. 4D shows localization of SLPI protein in breast cancer cells. Images were taken using an Olympus U-TBI90 microscope with 60× Objective. The images show immunostaining with anti-SLPI antibodies (red) and DAPI (blue).

To confirm that SLPI could also be detected in the nucleus of cancer cells, breast cancer cells were immunostained with anti-SLPI antibody, as shown in FIG. 4D. High-magnification confocal microscopy revealed that SLPI protein was present not only in the cytoplasm but also in the nucleus of TNBCs. This suggested that SLPI is available to bind nuclear Rb protein, potentially contributing to its regulation.

Figures 5A, 5B, 5C:
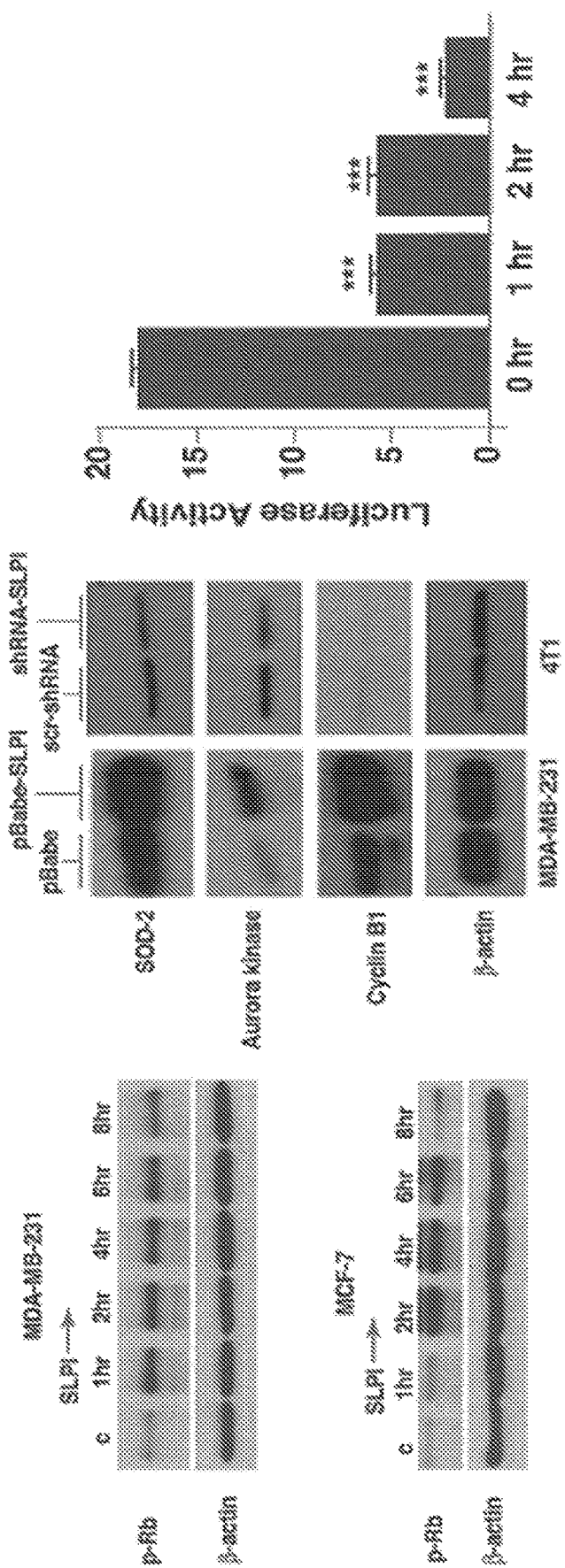
FIG. 5A shows SLPI activated Rb phosphorylation within 1-2 h. MD-MB-231 and MCF7 cells were exposed to recombinant SLPI protein (1.5 µg/mL); proteins obtained from these cells were subjected to gel electrophoresis and Western Blot analysis using antibodies directed against phospho-Rb and f-actin as a loading control. In a time dependent manner, SLPI activated Rb phosphorylation. Compound C74 repressed Rb phosphorylation. MD-MB-231 and MCF7 cells were treated with 1 µM of C74 for 16 h.
FIG. 5B shows the dynamics of SLPI-induced disruption of the physical interaction between Rb and FoxM1. Using a mammalian two-hybrid system with a pair of pBIND-Rb and pACT-FoxM1 fusion proteins with HEK293T cells, the dynamics of binding of Rb to FoxM1 was measured following recombinant SLPI protein treatment. SLPI was added to cell media in concentration of 1.5 µg/mL.
FIG. 5C shows that expression of FoxM1 target genes correlate with SLPI level. Western blotting was performed with lysed proteins from MDA-MB-231 cells overexpressing SLPI (pBabe-SLPI), compared to control (pBabe). SLPI was silenced in 4T1 cells using shRNA SLPI lentiviruses and compared to control cells with scr-shRNA lentiviruses. FoxM1 target genes—cyclin B1, aurora kinase B and superoxide dismutase-2 (SOD-2)—were up-regulated in cells with SLPI overexpression and down-regulated if SLPI was suppressed by shRNA.
Figure 6C:
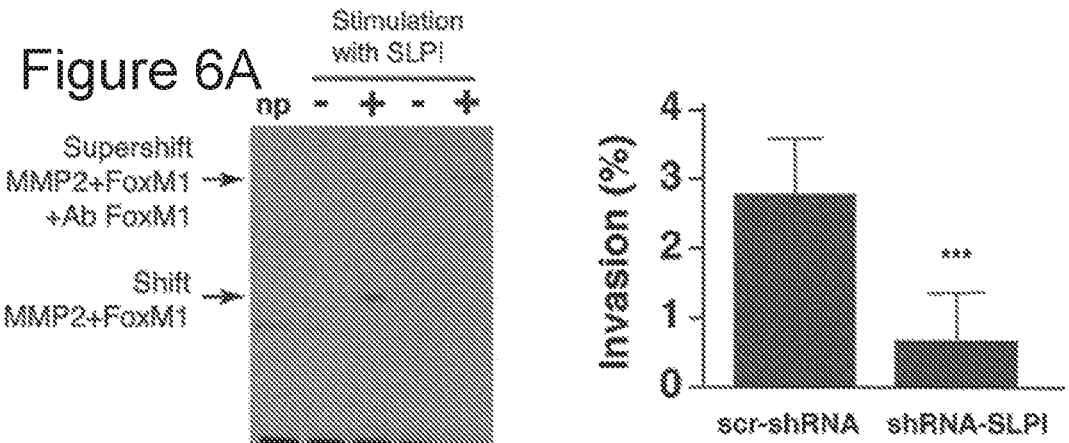
FIG. 6C shows a schematic representation of SLPI's effects on the regulation of the Rb/FoxM1 complex. In the presence of low levels of SLPI, Rb protein binds to FoxM1 and represses the activity of this transcriptional factor. Inhibition of FoxM1 leads to repression of FoxM1 target genes that are associated with tumor growth and metastasis. In cancer cells that express high levels of SLPI, it physically interacts with Rb to facilitate Rb release from FoxM1. This makes FoxM1 available to initiate transcription of target genes involved in tumor growth and metastasis.
Figure 6C:
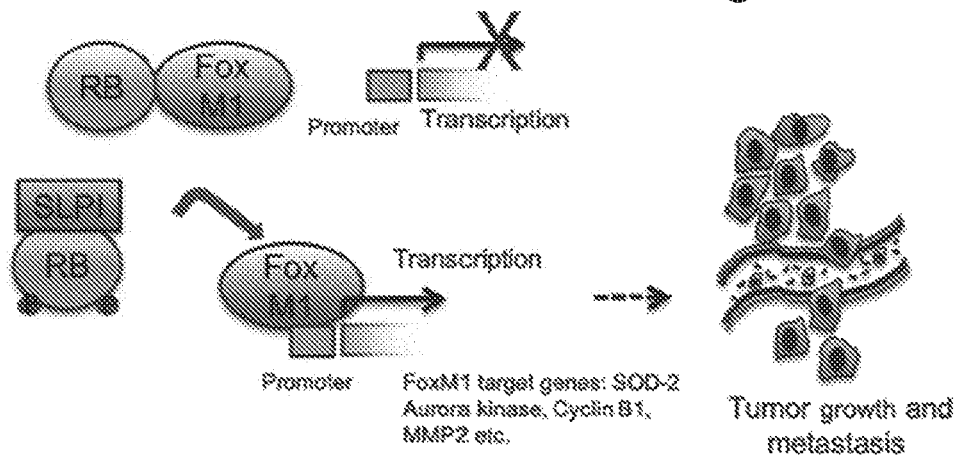

Several cell lines were then treated with recombinant SLPI protein and analyzed the phosphorylation status of Rb, as shown in FIG. 5A; there was increased phosphorylation of Rb as early as 1-2 h post treatment and this phosphorylation pattern persisted for a few hours. Treatment with compound C74 decreased phosphorylation of Rb in breast cancer cells, as shown in FIG. 5A. Since it had been shown that phosphorylation of Rb leads to its release from FoxM1 binding (see e.g., Kalinichenko et al, *Genes Dev.* 2004, 18:830-850; and Wierstra & Alves, *Biol. Chem.* 2006, 387: 949-962), the mammalian two-hybrid system was then used to confirm the effect of SLPI on the dynamics of the Rb-FoxM1 interaction. Cells containing a pair of GAL4-Rb and VP16-FoxM1 fusion proteins were treated with SLPI recombinant protein and demonstrated a progressive decrease of reporter construct activation, as shown in FIG. 5B. The dynamics of this process after SLPI treatment was similar to that of the Rb phosphorylation, as shown in FIG. 5A, thus suggesting the interconnection between these two events. FIG. 6C summarizes a potential molecular mechanism of FoxM1 activation through the interaction of Rb with SLPI.

To identify FoxM1-dependent molecular events occurring with modified SLPI expression, the latter protein was overexpressed in MDA-MB-231 cells and performed a series of immunoblotting experiments. It was discovered that overexpression of SLPI led to increased levels of known FoxM1 target proteins, such as cyclin B1, aurora kinase B, and superoxide dismutase-2 (SOD-2), as shown in FIG. 5C. To confirm this dependence, 4T1 cells were infected with SLPI shRNA lentiviruses. Down-regulation of the SLPI protein decreases expression of these FoxM1 target genes, as shown in FIG. 5C. These results collectively show that the level of SLPI protein correlates with FoxM1 transcriptional activity.

Example 7. In Vitro Invasion Assay

To determine whether SLPI promotes metastasis with enhancing vasoinvasive properties of cancer cells, a transwell cell migration and invasion assay was used (see e.g., Gunawardane et al, *Cancer Res.* 2005, 65:11572-11580). Fluoroblok transwell inserts (8 μm pore, Falcon) were coated with 0.1% gelatin (Sigma) before seeding $1 \times 10^5$ human umbilical vein endothelial cells (HUVEC) onto the polystyrene membrane. 4T1-GFP tumor cells that seeded on and invaded through the endothelial monolayer were analyzed in 24 h to quantify the percent of invading cells.

It was found that shSLPI-treated 4T1 cells exhibited a significant reduction in their invasive capability despite no change in the rate of proliferation, as shown in FIG. 6B. These data indicate that the vasoinvasiveness of 4T1 cancer cells was at least partially dependent on SLPI signaling.

Example 8. Electrophoretic Mobility Shift Assay

To directly test the ability of SLPI to modify FoxM1 binding to another target gene, MMP2, we used the electrophoretic mobility shift assay. Electrophoretic mobility shift assays (EMSAs) were performed following manufacture protocol using kit from Thermo Fisher. Double-stranded oligonucleotides from MMP2 promoter with FoxM1 binding site were used: 5'-CTGTTCAAGATG-GAGTCGCTCTGGTTC-3' (SEQ ID NO: 1). End-labelled DNA was detected using streptavidin-conjugated horseradish peroxidase. For the supershift assay, antibody against FoxM1 (Cell Signaling) was added to the binding reaction for 1 hour on ice.

The MMP2 promoter sequence comprising the FoxM1-binding site (−662 to −671 bp) was biotin-labeled and used as a probe for the protein binding gene promoter region (see e.g., Dai et al, *Oncogene,* 2007, 26:6212-6219). The probe was incubated with protein extracts from SLPI-treated MDA-MB-231 cells and untreated cells. This experiment demonstrated that SLPI induced protein binding to the probe, as reported by the retardation of its mobility (shift of bands in lane 3 vs. lane 2), as shown in FIG. 6A. Thus treatment of cells with SLPI resulted in a substantial increase in binding activity of FoxM1. The binding of this protein to the probe was sequence-specific, as it was blocked by competition with an unlabeled FoxM1 oligomer. To confirm that FoxM1 bound to MMP2 promoter in the presence of SLPI, a supershift assay was performed by adding FoxM1-binding antibody to that protein-DNA complex. The enhanced probe retardation is shown in lane 5 in FIG. 6A. This assay showed that FoxM1 binds to the MMP2 promoter and that SLPI stimulates FoxM1 binding activity (see FIG. 6A).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of inhibiting metastasis of a cancer associated with abnormal levels or expression of secretory leukocyte protease inhibitor in a subject, the method comprising administering to the subject a compound of Formula I:

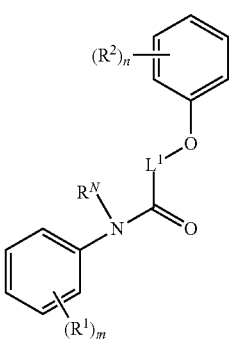

I or a pharmaceutically acceptable salt thereof, wherein:

$R^N$ is selected from the group consisting of H and $C_{1-6}$ alkyl;

$L^1$ is a $C_{1-6}$ alkylene group;

each $R^1$ is independently selected from the group consisting of $C(O)R^a$ and $C(O)OR^a$;

each $R^a$ is independently from $C_{3-6}$ alkyl;

each $R^2$ is independently selected from the group consisting halo, $C_{1-6}$ alkyl, $C_{1-6}$ haloalkyl, and $C_{1-6}$ alkoxy;

m is 1 or 2; and n is 1 or 2.

2. A method of treating a cancer associated with abnormal levels or expression of secretory leukocyte protease inhibitor in a subject, the method comprising administering to the subject a compound of Formula I:

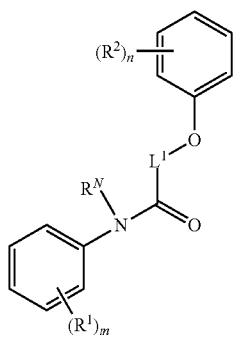

or a pharmaceutically acceptable salt thereof, wherein:
$R^N$ is selected from the group consisting of H and $C_{1-6}$ alkyl;
$L^1$ is a $C_{1-6}$ alkylene group;
each $R^1$ is independently selected from the group consisting of $C(O)R^a$ and $C(O)OR^a$;
each $R^a$ is independently from $C_{3-6}$ alkyl;
each $R^2$ is independently selected from the group consisting halo, $C_{1-6}$ alkyl, $C_{1-6}$ haloalkyl, and $C_{1-6}$alkoxy;
m is 1 or 2; and
n is 1 or 2.

3. The method of claim 1, wherein the cancer is selected from breast cancer, lung cancer, gastric cancer, and colorectal cancer.

4. The method of claim 1, wherein $R^N$ is H.

5. The method of claim 1, wherein $L^1$ is a $C_{1-3}$ alkylene group.

6. The method of claim 1, wherein $L^1$ is methylene.

7. The method of claim 1, wherein each $R^1$ is $C(O)OR^a$.

8. The method of claim 1, wherein each $R^1$ is selected from $C(O)CH_2CH_2CH_3$ and $C(O)CH_2CH_2CH_2CH_3$.

9. The method of claim 1, wherein each $R^2$ is independently selected from halo and $C_{1-6}$ alkoxy.

10. The method of claim 1, wherein each $R^2$ is independently selected from halo and $C_{1-3}$ alkoxy.

11. The method of claim 1, wherein each $R^2$ is independently selected from chloro and methoxy.

12. The method of claim 1, wherein m is 1.

13. The method of claim 1, wherein n is 1.

14. The method of claim 1, wherein the compound of Formula I is a compound of Formula II:

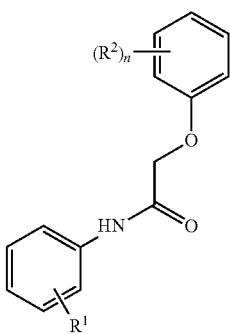

or a pharmaceutically acceptable salt thereof.

15. The method of claim 1, wherein the compound of Formula I is selected from the group consisting of:

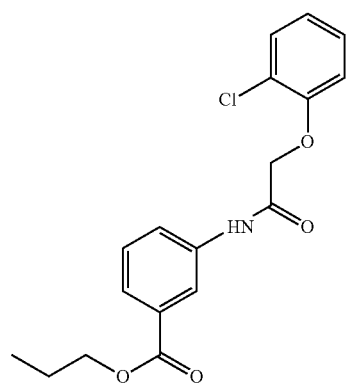 [SMILES: CCCOC(=O)c1cccc(NC(=O)COc2ccccc2Cl)c1]

,

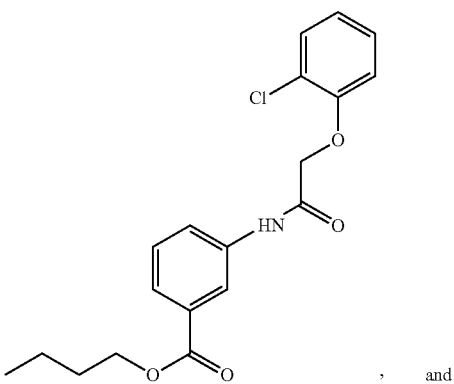

, and

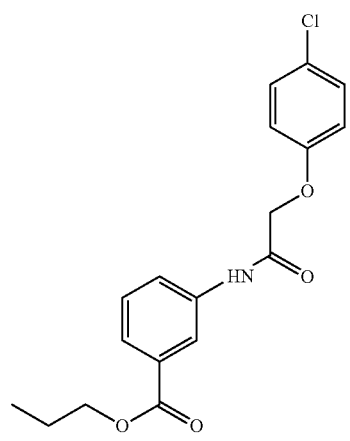

;

or a pharmaceutically acceptable salt thereof.

16. The method of claim 1, wherein the compound of Formula I is:

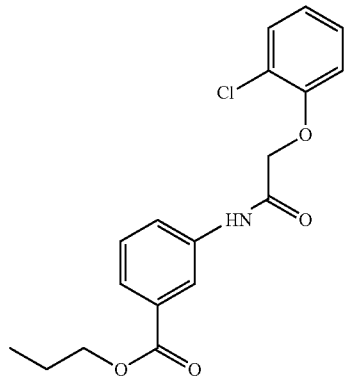

or a pharmaceutically acceptable salt thereof.

17. A method of inhibiting metastasis of triple negative breast cancer in a subject, comprising administering to the subject a compound which is:

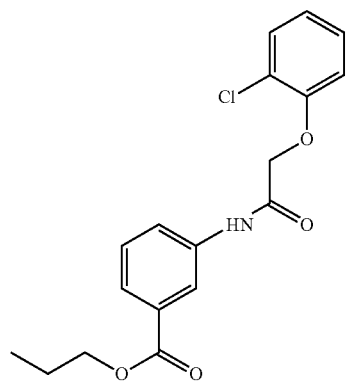 [SMILES: CCCOC(=O)c1cccc(NC(=O)COc2ccccc2Cl)c1]

or a pharmaceutically acceptable salt thereof.

18. The method of claim 1, further comprising administering to the subject one or more additional therapeutic agents.

* * * * *

UNITED STATES PATENT AND TRADEMARK OFFICE
CERTIFICATE OF CORRECTION

PATENT NO. : 11,351,144 B2
APPLICATION NO. : 16/754912
DATED : June 7, 2022
INVENTOR(S) : Igor Garkavtsev and Rakesh K. Jain It is certified that error appears in the above-identified patent and that said Letters Patent is hereby corrected as shown below:

In the Claims

In Column 28, Line 56, Claim 1, after "independently" insert -- selected --

In Column 28, Line 60, Claim 1, delete "$C_{1-6}$alkoxy;" and insert -- $C_{1-6}$ alkoxy; --

In Column 29, Line 23, Claim 2, after "independently" insert -- selected --

In Column 29, Line 26, Claim 2, delete "$C_{1-6}$alkoxy;" and insert -- $C_{1-6}$ alkoxy; --

Signed and Sealed this
Twenty-eighth Day of February, 2023

Katherine Kelly Vidal
*Director of the United States Patent and Trademark Office*